United States Patent
Snape et al.

(10) Patent No.: US 9,651,461 B2
(45) Date of Patent: May 16, 2017

(54) METHOD FOR WASHING ROCK SAMPLES

(75) Inventors: Michael Gerard Snape, Chester (GB); Rae Jones, South Wales (GB)

(73) Assignee: Rockwash Prep & Store Ltd, Caerphilly, Gwent (GB)

( * ) Notice: Subject to any disclaimer, the term of this patent is extended or adjusted under 35 U.S.C. 154(b) by 301 days.

(21) Appl. No.: 13/073,427

(22) Filed: Mar. 28, 2011

(65) Prior Publication Data

US 2012/0234360 A1      Sep. 20, 2012

(30) Foreign Application Priority Data

Mar. 18, 2011   (GB) .................................. 1104654.7

(51) Int. Cl.
*B08B 3/02*   (2006.01)
*G01N 1/34*   (2006.01)
*E21B 21/06*   (2006.01)

(52) U.S. Cl.
CPC ............... *G01N 1/34* (2013.01); *B08B 3/022* (2013.01); *E21B 21/066* (2013.01)

(58) Field of Classification Search
CPC ........ G01N 1/34; G01N 33/24; G01N 33/241; E02D 1/04; E02D 1/025; E02D 1/00; E21B 49/00; E21B 21/065; E21B 21/066; B08B 3/02; B08B 3/04; A47L 15/241; A47L 15/247; A47L 15/248; A47L 2401/20; A47L 2401/28; A47L 2501/24
(Continued)

(56) References Cited

U.S. PATENT DOCUMENTS 3,693,951 A * 9/1972 Lawhon ................ E21B 41/005
                                                    110/221
4,788,732 A * 12/1988 Kollmar .................. B08B 3/022
                                                    68/205 R
(Continued)

FOREIGN PATENT DOCUMENTS

CN           2109437 U       7/1992
FI    WO 0053076 A1 *    9/2000    ......... A47L 15/0047
(Continued)

OTHER PUBLICATIONS

Processing and Storage, Well Sample and Core Library, Kentucky Geologic Survery. Jul. 25, 2008. <http://www.uky.edu/KGS/core_library/processing.htm>. Retrieved via Wayback Machine on Sep. 7, 2105. https://web.archive.org/web/20080725103420/http://www.uky.edu/KGS/core_library/processing.htm.*
(Continued)

*Primary Examiner* — Katelyn Whatley
(74) *Attorney, Agent, or Firm* — Colin P. Cahoon; Celina M. Orr; Carstens & Cahoon, LLP (57) ABSTRACT

A method and an associated apparatus for washing rock samples, which is particularly suited to the washing and preparation of rock samples obtained from oil and gas wells. In one embodiment there is provided a method of washing rock samples involving a plurality of discrete rock samples; providing a plurality of sequentially arranged discrete washers each of which is spaced from a respective washing position and configured to direct a washing flow of water towards said washing position; and automatically conveying said samples relative to said washers so that each sample moves in succession through said washing positions for sequential washing by each said washer.

17 Claims, 4 Drawing Sheets

(58) Field of Classification Search
USPC .... 134/10, 25.1, 25.5, 40, 60, 61, 66, 104.4, 134/109, 110, 111, 124, 131, 135, 198, 134/199; 210/522, 513, 515, 922; 73/152.01–152.62
See application file for complete search history.

(56) References Cited

U.S. PATENT DOCUMENTS

| | | | | |
|---|---|---|---|---|
| 5,054,506 | A | | 10/1991 | Shakeri |
| 5,173,122 | A | * | 12/1992 | Tilby .................. A23N 12/023 127/2 |
| 5,401,320 | A | * | 3/1995 | Staples .................... B09C 1/02 134/10 |
| 5,453,133 | A | * | 9/1995 | Sparks et al. ................ 134/25.1 |
| 6,301,930 | B1 | * | 10/2001 | Warner .................... B08B 3/02 134/129 |
| 2007/0034240 | A1 | | 2/2007 | Berner et al. |
| 2011/0277798 | A1 | * | 11/2011 | Hillier .......................... 134/135 |
| 2012/0103077 | A1 | * | 5/2012 | Koshnick .............. G01N 33/24 73/64.56 |

FOREIGN PATENT DOCUMENTS

| | | | |
|---|---|---|---|
| JP | 56013051 A | | 2/1981 |
| JP | 09196558 A | * | 7/1997 ............. F26B 11/08 |
| JP | 2003251330 A | | 9/2003 |
| WO | 87/04790 | | 8/1987 |

OTHER PUBLICATIONS

UK Search Report for related Application GB1104654.7, performed on Aug. 4, 2011.
PCT International Search Report and Written Opinion for PCT/GB2012/000182 issued on May 16, 2012.

* cited by examiner

METHOD FOR WASHING ROCK SAMPLES

BACKGROUND OF THE INVENTION

The present invention relates to a method and an associated apparatus for washing rock samples, and is particularly suited to the washing and preparation of rock samples obtained from oil and gas wells.

DESCRIPTION OF THE PRIOR ART

The importance and value of geological data derived from rock-samples retrieved from oil & gas drilling operations has increased tremendously in recent years. This reflects the inflated costs of global drilling operations, particularly in new and challenging environments, such as ultra-deep water and difficult onshore areas. The speed and quality of well data generation is a key commercial factor because multi-million dollar drilling decisions are being made on the basis of the new geological data generated from these rock samples.

Needless to say, health and safety remains paramount for the oil and gas companies around the world. Furthermore, in recent years, environmental considerations of the drilling process and subsequent geological analysis has come under considerable scrutiny by the world at large.

Rock samples from oil and gas wells are generated during the drilling process. The drill bit cuts and grinds rocks as the well-bore penetrates the geological strata at depth, pulverising the strata into small rock fragments. These small rock fragments are commonly referred to as "ditch-cuttings" or just "cuttings. At set intervals, these ditch-cuttings are circulated from the bottom of the well to the surface, by suspension within the circulating "drilling mud" which acts as a drilling lubricant within the well. The resulting ditch-cuttings samples therefore arrive at the surface as dirty fragments of rock covered in drilling mud.

On occasion, a drilling company might recover whole-core samples in the form of long cylindrical lengths of cored rock, or side-wall core samples from the same well bore. However, as drilling costs continue to rise, there is a tendency to take these sorts of samples less frequently than has been the case in the past. This places greater emphasis on the preservation and analysis of the more commonly obtained ditch-cuttings samples from new and old archived wells alike.

Rock samples in the form of dirty ditch-cuttings thus commonly form the basis for subsequent geological analysis. There is therefore a need to clean these samples from all drilling contaminants, in order for important geological information to be derived. Also, after analysis the samples must be correctly and reliably labelled so that the well operator company and service companies studying the samples know the exact identity and location of the well from which the sample was taken, and the depth at which it was obtained.

Presently, rock samples obtained as ditch cuttings are washed manually using steel or brass sieves. Each individual sample is placed in a respective sieve (typically approximately 20 cm in diameter) and run under a flow of fresh water from a shower head or the like. The sample is mixed with detergent and agitated by hand under the flow of water until the water runs clear through the base of the sieve. The washed sample is then transferred to an individual container for drying, either on a hotplate or in an oven.

As will be appreciated, the prior art washing method explained above is extremely labour-intensive and time consuming. This can be very limiting indeed when many samples are obtained from each well. For example, generally 300-500 individual rock samples are obtained from a single well, and sometimes this number can be as high as 900. Also, the prior art method is very wasteful of water.

SUMMARY OF THE INVENTION

It is an object of the present invention to provide an improved method for washing rock samples.

It is another object of the present invention to provide an improved apparatus for washing rock samples.

According to a first aspect of the present invention, there is provided a method of washing rock samples, the method comprising the steps of: providing a plurality of discrete rock samples; providing a plurality of sequentially arranged discrete washers each of which is spaced from a respective washing position and configured to direct a washing flow of water towards said washing position; and automatically conveying said samples relative to said washers so that each sample moves in succession through said washing positions for sequential washing by each said washer.

Preferably the method comprises the supply of substantially fresh water to at least one of said washers.

Advantageously, the method comprises the step of collecting water used to wash said samples in each said washing position and recirculating the water for supply to at least one of said washers.

Conveniently, said step of automatically conveying the samples relative to said washers comprises moving each said sample through the washing position associated with the or each washer supplied with recirculated water before the washing position associated with the or each washer supplied with fresh water.

Preferably a plurality of said washers are supplied with recirculated water, and a single washer is supplied with substantially fresh water.

Advantageously, the method further comprises the step of filtering said recirculated water prior to its supply to the or each said washer.

Conveniently, the method further comprises the step of passing said recirculated water over a weir prior to its supply to the or each said washer.

Preferably, each said sample remains in each said washing position for a predetermined washing period.

Advantageously, the method further comprises the step of RF tagging each sample.

Conveniently, the method further comprises the step of placing each said sample in a respective receptacle prior to said conveying step.

Preferably, each said receptacle takes the form of a sieve.

Advantageously, the method further comprises the step of drying each said sample after it has been conveyed through all of said washing positions and washed by the washers.

Conveniently, the method includes providing a plurality of sequentially arranged discrete dryers and automatically conveying said samples relative to said dryers so that each sample moves in succession through or past said dryers for sequential drying by each dryer.

Preferably, each said dryer comprises a heater arranged to direct heat towards a respective drying position, and each sample is automatically conveyed in succession through said drying positions.

Advantageously, each said heater comprises an infrared lamp.

Conveniently, each said sample remains in each said drying position for a predetermined drying period.

Preferably, each said predetermined drying period is equal in length to each said washing period.

Advantageously, the method further comprises the step of automatically agitating each sample as it is dried.

Conveniently, the method further comprises the step of photographing each sample after said drying step.

Preferably, the method further comprises the step of weighing each sample after said drying step.

Advantageously, the method further comprises the step of labelling each sample after said drying step.

According to another aspect of the present invention, there is provided an apparatus for washing rock samples, the apparatus comprising a plurality of sequentially arranged discrete washers, each of which is spaced from a respective washing position and configured to direct a washing flow of water towards said washing position; and a conveyor operable to automatically convey a plurality of discrete rock samples relative to said washers such that each sample moves in succession through said washing positions for sequential washing by each said washer.

Preferably, said plurality of washers comprise at least one washer that is connected to a supply of substantially fresh water so as to produce a washing flow of substantially fresh water.

Advantageously, said plurality of washers comprise at least one washer that is connected to a recirculated flow of water.

Conveniently, the or each said washer that is supplied with substantially fresh water is arranged sequentially after the or each washer that is supplied with recirculated water.

Preferably, the apparatus comprises a plurality of washers connected to said recirculated flow of water and a single washer connected to said supply substantially fresh water.

Advantageously, the apparatus further comprises at least one filter through which said recirculated flow of water passes.

Conveniently, the apparatus comprises a weir over which said recirculated flow of water passes.

Preferably, the apparatus further comprises a pump operable to pump said recirculating flow of water to said washers.

Advantageously, the apparatus further comprises a plurality of sequentially arranged discrete dryers and a conveyor operable to automatically convey said samples relative to said dryers such that each sample moves in succession through or past said dryers for sequential drying by each dryer.

Conveniently, each said dryer comprises a heater arranged to direct heat towards a respective drying position, and said conveyor is configured to move each sample in succession through said drying positions.

Preferably, each said heater comprises an infrared lamp.

Conveniently, the apparatus further comprises agitating means operable to automatically agitate each sample as it is moved through said drying positions.

Preferably, the apparatus further comprises a plurality of receptacles, each receptacle being configured for the receipt of a respective sample, and wherein said agitating means comprises a mechanism operable to engage and oscillate said receptacles.

BRIEF DESCRIPTION OF THE DRAWINGS

So that the invention may be more readily understood, and so that further features thereof may be appreciated, embodiments of the invention will now be described by way of example with reference to the accompanying drawings in which.

DETAILED DESCRIPTION OF THE PREFERRED EMBODIMENTS

Figure 1:
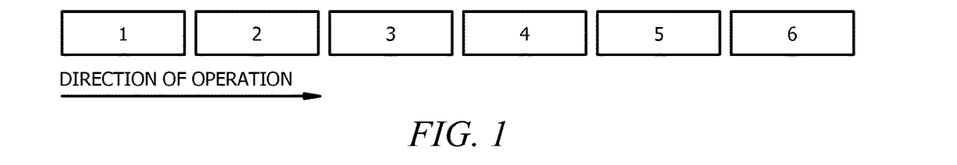
FIG. 1 is a flow diagram illustrating the principal steps in the method of the present invention.
Figure 2:
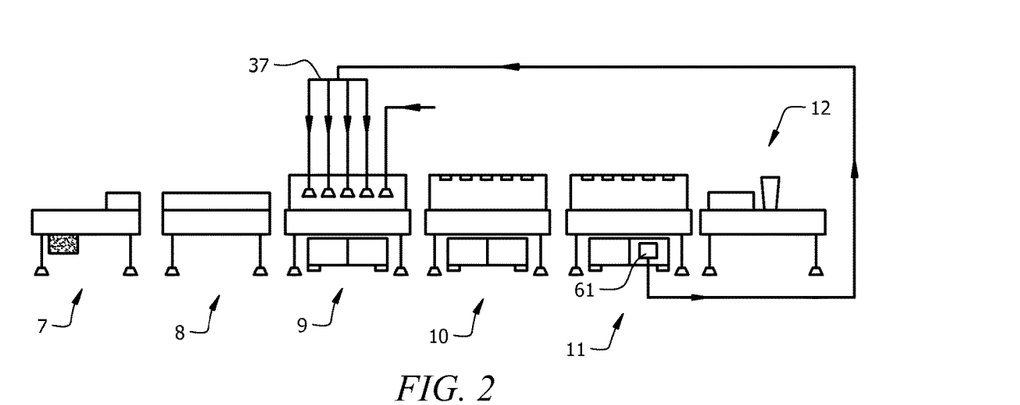
FIG. 2 is a schematic illustration showing a general layout of apparatus suitable for implementing the method steps of FIG. 1.

Turning now to consider the drawings in more detail, the method of the present invention comprises a number of successive stages or steps as illustrated schematically in FIG. 1, and which will be described in more detail below with specific reference to an embodiment of the apparatus. FIG. 2 shows a schematic representation of individual modules of the apparatus which correspond in their function to the stages or steps of the method denoted in FIG. 1.

Initially, a plurality of discrete rock samples are prepared for washing. This preparation stage of the method is illustrated schematically at 1 in FIG. 1, and is performed with the use of a preparation module 7 of the apparatus illustrated schematically in FIG. 2. When the samples have been prepared ready for washing in stage 1, they are arranged ready for washing in a feed stage of the method denoted at 2 in FIG. 1 using a feed module 8 illustrated in FIG. 2. The samples are then washed in a washing stage 3 of the method which is carried out via the use of a washing module 9 illustrated schematically in FIG. 2. Two drying stages 4, 5 then follow which are carried out via the use of respective drying modules 10, 11. Finally, the washed and dried samples are then recorded in a recording stage 6 of the method which is carried out with the use of a recording module 12 of the apparatus. As illustrated FIG. 1, the samples are processed through the above-mentioned stages of the method in sequence.

Figure 3:
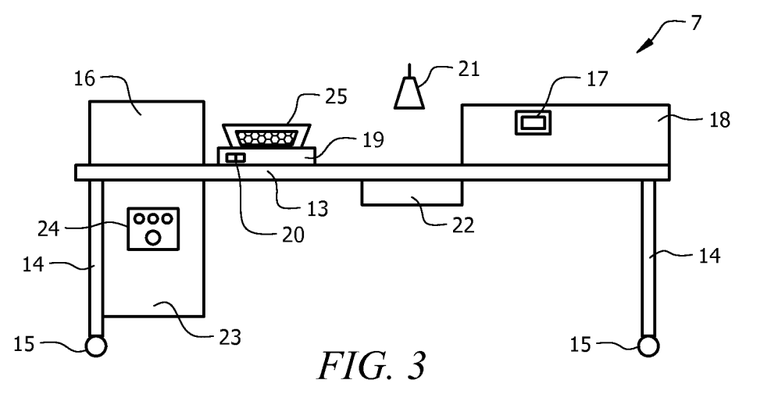
FIG. 3 is a schematic side elevational view of a sample preparation module of the apparatus.

FIG. 3 illustrates the preparation module 7 in more detail. The module 7 comprises a work-surface 13 which is supported at a convenient height above the ground by a plurality of legs 14 in the manner of a conventional table. The legs 14 each have a castor 15 or other wheel arrangement at their lower ends so that the module as a whole is moveable.

The work-surface 13 supports a computer 16 (which may take the form of a conventional desktop, laptop or notebook computer) having a memory, a display and an input keyboard. The computer 16 is operatively connected to an RFID reader 17 which is mounted to a housing 18. The housing has an internal recess (not shown) which is sized and configured to receive a support plate or the like which are used in the method to support individual samples. One such plate is illustrated schematically at 19 in FIG. 3. Each plate 19 carries a respective and individual RFID tag 20. The RFID reader mounted on the housing 18 is positioned to scan or otherwise identify the tags 20 of the plates as each plate is placed in or moved through the housing 18.

The preparation module 7 also includes a tap or shower head 21 which is supported above the work-surface 13 and which is connected to a supply of clean, and preferably warm water. A basin 22 is provided below the tap or shower head 21 and is supported below the work-surface 13.

The preparation module 7 also supports a control unit 23 having a control panel 24 and which serves to control the various functions of the modules of the apparatus. However, it is to be appreciated that the control module 23 does not have to be provided as part of the preparation module, and indeed could be mounted on any of the other modules in the apparatus, or indeed even remotely from the modules such as conveniently on a nearby wall.

The preparation stage 1 of the method involves initially taking a rock sample obtained from a well and entering data pertaining to the sample into the memory of the computer 16 via the keyboard. Such data might include, for example; details of the client or company whose well the sample was obtained from, the name or identifying code of the particular well, the depth from which the sample was taken, and details regarding the nature of the actual sample itself (for example: ditch cuttings, core, sidewall core, or field sample).

The sample itself is then crushed if necessary and soaked in warm water from the tap or shower head 21 to soften any adhering drilling mud. Detergent may be added to break down and remove any oil residue.

The sample is then poured into a sieve 25 and the sieve is placed on or engaged with a respective RF tagged support plate 19. The support plate and the sieve are then positioned over the basin 22 to permit excess water remaining on the sample to drain into the basin. As will be appreciated, the support plates 19 are thus each configured to permit the flow of water from top to bottom and may, for example, be generally annular in configuration and sized to receive a sieve 25 therein.

The sieve 25 and its associated support plate 19 are then pushed passed though the housing 18 and thus past the RFID reader 17 which identifies the tag 20 and passes that information to the computer. The computer 16 then automatically associates the data pertaining to the sample with the particular sieve 25 and sieve plate 19. Alternatively, the housing 18 could be configured to store a plurality of plates 19, for example in a stack, with its RFID reader 17 positioned to scan or otherwise identify the tag 17 of each plate 19 as it is removed from the stack inside.

Figure 4:
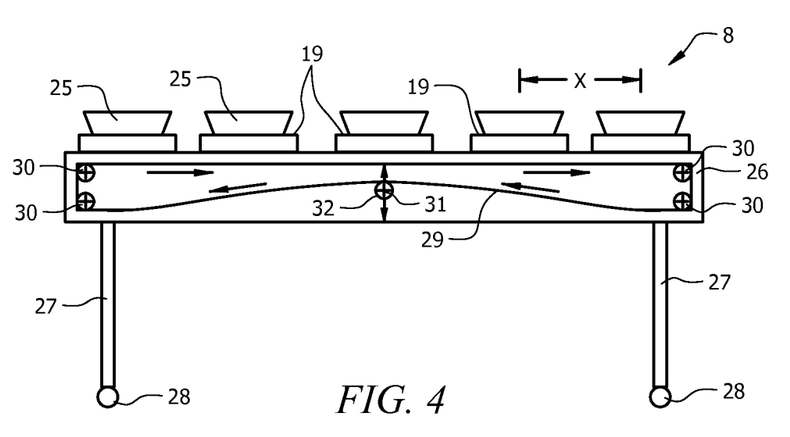
FIG. 4 is a schematic side elevational view of a sample feed module of the apparatus.

The sample, provided within its individual sieve 25 and supported on a tagged plate 19 is then passed from the preparation module 7 to the feed module 8 ready for the feed stage 2 of the method.

The feed module 8 is illustrated in more detail in FIG. 4. The module 8 comprises a conveyor housing 26 which is supported above the ground by legs 27 on castors 28 in a similar manner to the preparation module 7. The conveyor housing 26 houses a conveyor mechanism comprising one or more conveyor belts or chains 29 arranged to run continuously around guide and/or drive sprockets 30 mounted for rotation relative to the housing 26. The conveyor mechanism further includes a rotatable tensioning sprocket 31 which is mounted for sliding movement in a vertical sense relative to the housing 26 as denoted by arrow 32. The tensioning sprocket is biased upwardly and the lower run of the or each belt or chain 29 engages and runs over the tensioning sprocket 32 in a manner known per se.

The conveyor housing 26 is substantially open at its top, or at least comprises one or more apertures such that the conveyor chains or belts are exposed from above. Furthermore, the feed module 8 is configured such that the upper run of the conveyor belts or chains 29 is at least approximately level with the work-surface 13 of the preceding preparation module. Also, as illustrated in FIG. 2, the feed module 8 is positioned generally adjacent the preparation module 7.

As indicated above, when each sample has been prepared in accordance with the preparation stage 1 of the method it is passed to the feed module 8. More particularly, a plurality of said samples are prepared in succession, and each is passed to the feed module such that the support plate 19 of each sample is placed on the upper run of the conveyor chains or belts 29. FIG. 4 illustrates five such samples, in their respective sieves 25 and supported on their respective plates 19 placed on the conveyor. As illustrated, the sieves 25 and associated plates 19 are each positioned in spaced relation to one another, to form a queue of samples sitting on the conveyor 29. The sieves and support plates are actually spaced from one another by a predetermined approximate distance, as will be explained below.

Operation of the conveyor mechanism is controlled automatically by the control unit 23 upon receipt of a start signal from the control panel 24. The conveyor mechanism is operated under the control of the control unit 23 to advance the conveyor 29 in a step-wise manner. More particularly, the conveyor is operated to move an index distance (denoted x in FIG. 4) over the sprockets 30 in the direction indicated in FIG. 4, and thus to move the samples in their respective sieves 25 to the right (as illustrated) by an equal amount. The conveyor then stops and remains stationary for a predetermined dwell period, after which the conveyor then moves again by a further, equal index distance. In a preferred embodiment, the control unit 23 is configured to make each dwell period approximately equal to one minute. However, it is proposed to make the dwell period adjustable, for example via the control unit 24, to enable an operator to set any convenient dwell period.

As will thus be appreciated, the feed module 8 is operable to feed the samples, in their respective sieves 25 and with their associated support plates 19 towards the washing module 9 in succession, and at predetermined time intervals from one another.

Figure 5:
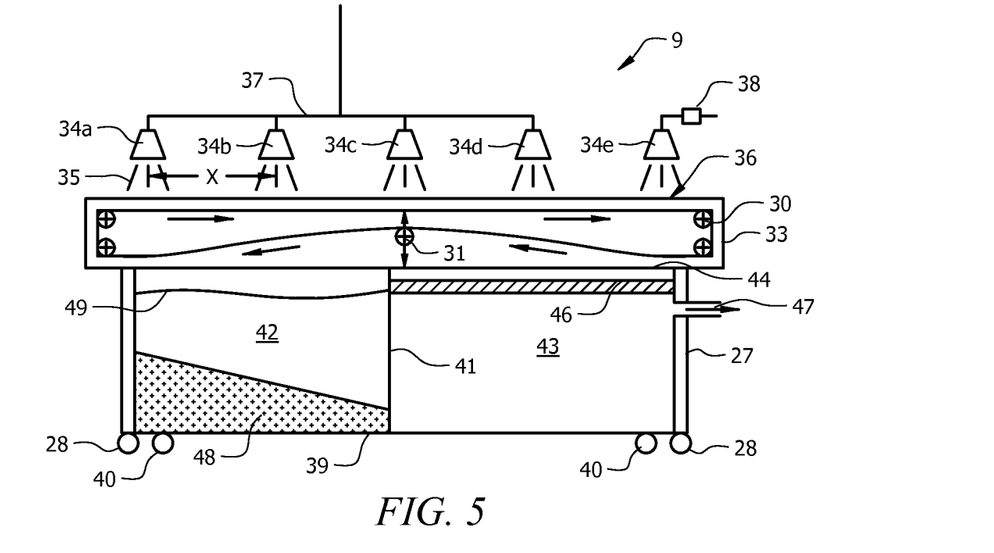
FIG. 5 is a schematic side elevational view of a washing module of the apparatus.

The washing module 9 is illustrated in more detail in FIG. 5. The module comprises a conveyor housing 26 of substantially identical form to the conveyor housing of the preceding feed module 8. The conveyor housing 26 is again supported above the ground by legs 27 on castors 28, and houses a conveyor mechanism which is also of substantially identical form to that of the feed module 8.

Above the conveyor housing 26, there is supported an array of discrete washers 34. Each washer 34 preferably takes the form of a shower head supported above the upper run of the conveyor and configured to direct a washing flow of water 35, preferably downwardly, towards a respective washing position 36 on the conveyor 29. The washers 34 are arranged sequentially and are substantially equi-spaced from one another by a distance substantially equal to the aforementioned index distance x.

The arrangement illustrated in FIG. 5 comprises five such washers. The first four of the washers 34a, 34b, 34c, 34d, as considered relative to the advance direction of the conveyor (left to right in FIG. 5) are fluidly connected by appropriate pipework 37 to a supply of recirculated water, as will be described in more detail below. However the final washer 34e in the sequence, (i.e. the last washer as considered relative to the advance direction of the conveyor 29) is fluidly connected to a supply of substantially fresh water. In this context, fresh water is considered to represent water which is substantially clean and free from contaminants and which has not been used previously to wash any rock samples in the method of the invention. In preferred embodiments, the fresh water washer 34e is connected to a mains supply of fresh water, the flow of which is controlled by a flow control arrangement 38 which may comprise, for example, a flow sensor, a timer and a solenoid-operated valve (not shown).

The washing module 9 further comprises a removable effluent tank 39 which, in use, is positioned below the conveyor housing 26 to catch water and effluent falling downwardly from the washing positions 36. The effluent tank is mounted for movement on castors 40 and is received between the legs 27 supporting the conveyor housing 26. Approximately halfway along the length of the tank 39, there is provided an internal weir 41, which extends vertically upwardly from the base of the tank and which terminates at a position generally below the tensioning sprocket 31 of the conveyor mechanism when the tank is installed in its in-use position illustrated in FIG. 5. The weir 41 thus effectively divides the tank into two chambers; a first chamber 42 located to the left in FIG. 5, and a second chamber 43 located to the right in FIG. 5.

The first chamber 42 is open at the top, but the second chamber 43 is closed by a cover 44. A filter 46, preferably formed of foam, extends across the top of the second chamber 43 just below the level of the top of the weir 41. The second chamber 43 also has a fluid outlet 47 at its end remote from the first chamber 42.

Operation of the washing module 9 is controlled by the control unit 23. More particularly, the conveyor mechanism of the washing module is operated to advance the conveyor 29 in a step-wise manner in synchronism with the conveyor of the preceding feed module 8. The conveyor of the washing module 9 is thus also moved by index distances x between successive dwell periods. Thus, in the preferred operating regime the conveyor 29 is advanced so as to move each discrete rock sample, in turn, through each of the washing positions 36 under the respective washers 34, and to position each sample under a successive washer during each dwell period (preferably one minute). As will thus be appreciated, when the samples, in their respective sieves 25, are positioned beneath the washers, the flow of washing water downwardly from the washers serves to wash the samples. The washers can be operated in synchronism with the conveyor so as only to permit the flow of washing water 35 when the conveyor is stationary with the samples located in washing positions beneath respective washers 34. However this is not essential, and indeed the system could instead be operated with substantially continuous flow of water through the washers 34.

As each sample advances through the washing module, it is washed, in turn, by the water flowing from each washer 34. As will be appreciated, the most effluent is thus produced from the first washer 34a in the sequence, and the samples each become gradually cleaner as they move though the module.

The excess water and effluent washed from the samples by the first and second washers 34a, 34b falls vertically downwardly directly into the first chamber 42 of the effluent tank, to the left of the weir, where solid constituents of the effluent builds up as a deposit 48. The water and effluent produced from the samples as they are washed by the subsequent washers 34c, 34d, 34e, is blocked from falling into the second chamber by the cover 44 and so is also directed into the first chamber 42. As will be appreciated, the weir 41 maintains a constant water level 49 in the first chamber and permits the flow of excess water over the weir, and into the second chamber 43. This water flowing over the weir 41 passes through the filter 46 and is thus filtered. The water flowing into the second chamber then flows out through the fluid outlet 47.

Because the effluent tank is mounted on castors 40 it can be conveniently rolled out from its in-use position beneath the conveyor housing 26 for periodic emptying of deposit 48 and cleaning of the filter 46.

After being washed by each washer 34, each sample is then transferred by the conveyor 29 to the first drying module 10 which, as illustrated in FIG. 2, is positioned immediately adjacent the washing module 9 as the next module in the sequence.

The first drying module 10 is illustrated in more detail in FIG. 5. The module comprises a conveyor housing 26 of substantially identical form to the conveyor housing of the preceding washing module 9 and the feed module 8. The conveyor housing 26 is again supported above the ground by legs 27 on castors 28, and houses a substantially identical conveyor mechanism.

Figure 6:
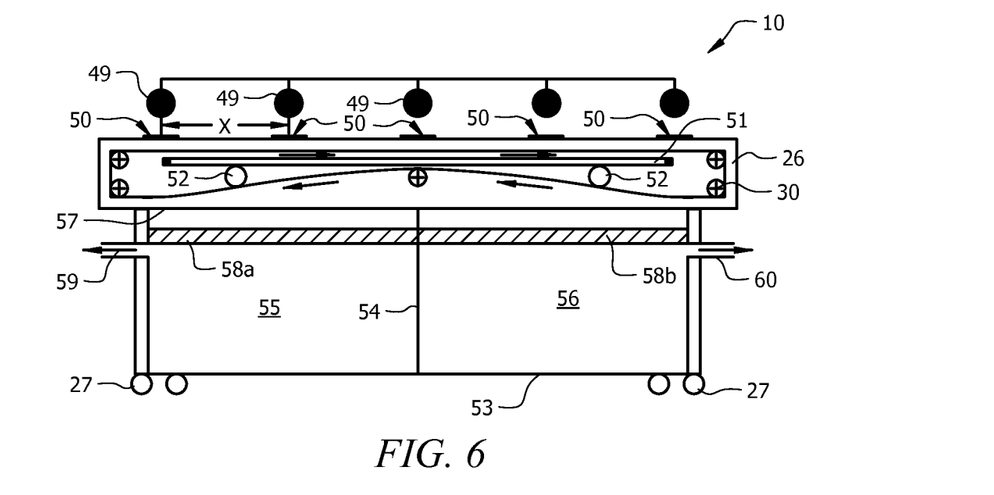
FIG. 6 is a schematic side elevational view of a first drying module of the apparatus.

Above the conveyor housing 26, there is supported an array of discrete dryers 49. Each washer 49 preferably takes the form of an infrared lamp supported above the upper run of the conveyor and configured to radiate heat downwardly towards a respective drying position 50 on the conveyor 29. The dryers 49 are arranged sequentially and are substantially equi-spaced from one another by a distance substantially equal to the aforementioned index distance x.

The first drying module additionally comprises a mechanism for agitating rock samples, in their respective sieves 25, as they are advanced through the module by the conveyor 29. The agitation mechanism can take any convenient form and may comprise, for example, one or more agitating bars 51 arranged immediately below the upper run of the conveyor 29 and arranged to engage the supporting plates 19 associated with the samples as they move through the module. The or each agitating bar is mounted for oscillating movement, for example under the action of an offset cam mechanism (not shown).

Additionally, the conveyor housing 26 of the first drying module 10 is provided with one or more extraction ports 52 for fluid connection to an extractor fan to pull a flow of drying air across or over the drying positions 50.

The first drying module 10 further comprises a removable filtration tank 53 which, in use, is conveniently positioned below the conveyor housing 26. The filtration tank 53 is similar in form to the effluent tank 39 of the preceding washing module 9 and so is again mounted for movement on castors 40 and is received between the legs 27 supporting the conveyor housing 26. The filtration tank 53 again includes an internal weir 54 which divides the tank into two chambers; a first chamber 55 located to the left in FIG. 6, and a second chamber 56 located to the right in FIG. 6. However, in this arrangement, both chambers closed across the top by a cover 57, and each chamber has a respective filter 58a,b extending below the level of the top of the weir 54. In this module, the first chamber 55 of the tank has a fluid inlet 59. The fluid inlet 59 is fluidly connected to the fluid outlet 47 of the preceding washing module, and is thus arranged to receive a flow of water directed into the chamber 55 from the chamber 43 of the washing module 9. The second chamber 56 of the first drying module 10 has a fluid outlet 60 of substantially identical form to the fluid outlet 47 of the preceding washing module 9.

Operation of the first drying module 10 is controlled by the control unit 23. More particularly, the conveyor mechanism of the drying module is operated to advance the conveyor 29 in a step-wise manner in synchronism with the conveyors of the preceding washing module 9 and the feed module 8. The conveyor of the drying module 10 is thus also moved by index distances x between successive dwell periods. Thus, in the preferred operating regime the conveyor 29 is advanced so as to move each discrete rock sample, in turn, through each of the drying positions 50 under the respective dryers 49, and to position each sample under a successive dryer during each dwell period (preferably one minute). As will thus be appreciated, when the samples, in their respective sieves 25, are positioned beneath the dryers the heat radiated downwardly from the dryers serves to dry the samples. Additionally, operation of the extractor fan (not shown) connected to the extraction ports 52 pulls a flow of drying air over the samples, and the agitation bars 51 serve to oscillate the sieves 25 and thus shake excess water from the samples therein. The dryers, agitator bars 51 and the extractor fan can all be operated in synchronism with the conveyor so as only to be energised when the conveyor is stationary with the samples located in drying positions 50 beneath respective dryers 49. However this is not essential, and indeed the system could instead be operated with substantially continuous energisation of the dryers 49, the agitation mechanism and the extractor fan.

As each sample advances through the drying module 10 it is dried, in turn, by the heat produced by each dryer 49.

The filtration tank 53 does not receive any water dried from the rock samples above. Instead, the filtration tank 53 simply serves to further filter, and hence cleanse, the water which was captured by the effluent tank 39 of the preceding module. As will be appreciated, the weir 54 maintains a constant water level in the first chamber 55, above the level of its filter 58a and permits the flow of excess water over the weir, and into the second chamber 56 through its filter 58b. The water thus flows through the filtration tank 53 from the preceding effluent tank 39, by passing upwardly through the first filter 58a, over the weir, and then passing downwardly through the second filter 58b. The water flowing into the second chamber then flows out through the fluid outlet 60.

Because the filtration tank is mounted on casters it can be conveniently rolled out from its in-use position beneath the conveyor housing 26 for periodic emptying of any build up of silt and for cleaning of the filter 46.

After being dried by each dryer, each sample is then transferred by the conveyor 29 to the second drying module 11 which, as illustrated in FIG. 2, is positioned immediately adjacent the first drying module 10 as the next module in the sequence.

Figure 7:
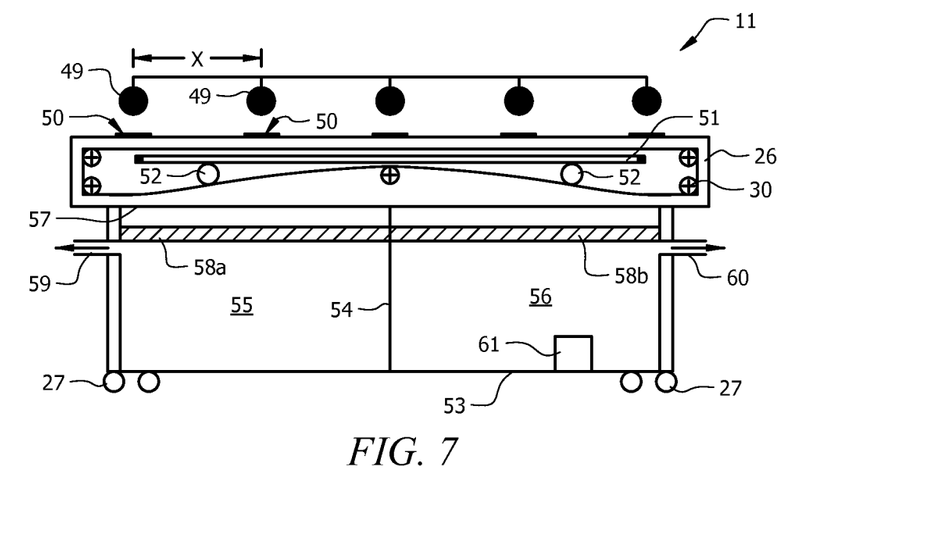
FIG. 7 is a schematic side elevational view of a second drying module of the apparatus.

The second drying module 11 is illustrated in more detail in FIG. 7, and as will be seen is substantially identical to the first drying module 10. The same reference numerals are thus used in FIG. 7 to denote identical or corresponding component parts of the second drying module 11. Operation of the second drying module 11 is also substantially identical to the manner in which the first drying module 10 is operated.

More particularly, the conveyor mechanism of the second drying module 11 is operated to advance the conveyor 29 in a step-wise manner in synchronism with the conveyors of the preceding first drying module 10, the washing module 9 and the feed module 8. The conveyor of the second drying module 11 is thus also moved by index distances x between successive dwell periods. Thus, in the preferred operating regime the conveyor 29 is advanced so as to move each discrete rock sample, in turn, through each of the drying positions 50 under the respective dryers 49, and to position each sample under a successive dryer during each dwell period (preferably one minute) in exactly the same manner as in the case of the preceding first drying module 10. As will thus be appreciated, when the samples, in their respective sieves 25, are positioned beneath the dryers the heat radiated downwardly from the dryers serves to dry the samples. Additionally, operation of the extractor fan (not shown) connected to the extraction ports 52 pulls a flow of drying air over the samples, and the agitation bars 51 serve to oscillate the sieves 25 and thus shake excess water from the samples therein. The dryers, agitator bars 51 and the extractor fan can all be operated in synchronism with the conveyor so as only to be energised when the conveyor is stationary with the samples located in drying positions 50 beneath respective dryers 49. However this is not essential, and indeed the system could instead be operated with substantially continuous energisation of the dryers 49, the agitation mechanism and the extractor fan.

As each sample advances through the second drying module 11 it is dried, in turn, by the heat produced by each dryer 49. After passing through both drying modules in this manner, each sample will thus have been dried by a total Of 10 discrete dryers 49 in succession.

It is significant to note that the fluid inlet 59 of the filtration tank 53 of the second drying module 11 is fluidly connected to the fluid outlet 60 of the filtration tank of the first drying module 10. Furthermore, in the case of the second drying module 11, the second chamber 56 of the filtration tank 53 does not have a fluid outlet in the same way that the filtration tank of the preceding first drying module 10 does. Instead, the second drying module 11 comprises a pump 61 which is arranged and operable to pump water out of the second chamber 56. Preferably, as illustrated in FIG. 11, the pump 61 takes the form of an immersion pump provided at the bottom of the second chamber 56.

As illustrated most clearly in FIG. 2, the pump 61 is fluidly connected via the pipework 37 to the first four washers 34a, 34b, 34c, 34d of the washing module 9. The pump 61 is thus operable to pump water from the second chamber 56 of the filtration tank 53 in the second drying module, in a recirculating manner back to the washers 34a-d of the washer module 9 and thus drives the flow of recirculated water to those washers. As already explained above, the fifth washer 34e of the washing module 9 is supplied with a flow of substantially fresh water, for example from a mains supply. As will thus be appreciated, the supply of fresh water to the fifth washer 34e in the sequence represents the sole input of fresh water into the system. The other four washers 34a-d are all supplied with water which has already been used to wash rock samples and which has been filtered and recycled via the effluent tank 39 and the two filtration tanks 53.

After being dried by each dryer 49 of the second drying module 11, each sample is then transferred by the conveyor 29 to the recording module 12 which, as illustrated in FIG. 2, is positioned immediately adjacent the second drying module 11 as the next module in the sequence.

Figure 8:
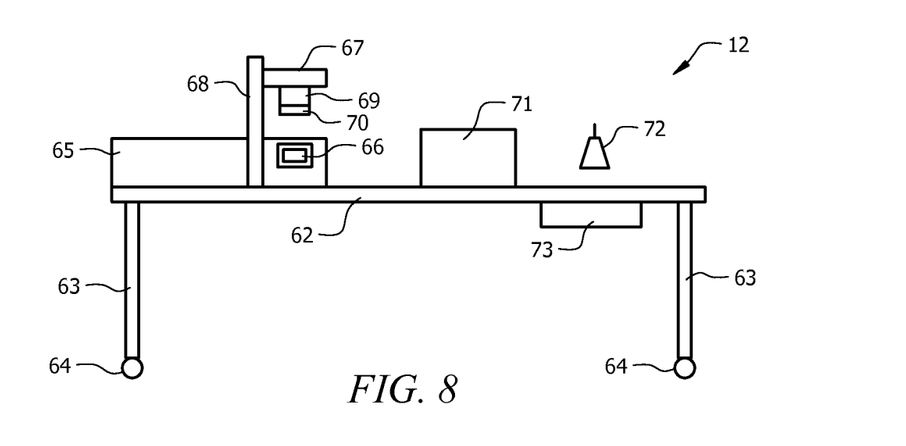
FIG. 8 is a schematic side elevational view of a recording module of the apparatus.

FIG. 8 illustrates the recording module 12 in more detail. The module 12 comprises a work-surface 62 which is supported at a convenient height above the ground by a plurality of legs 63 in the manner of a conventional table. The legs 63 each have a castor 64 or other wheel arrangement at their lower ends so that the module as a whole is moveable in the same manner as each of the preceding modules. The legs 63 support the work surface 62 above the ground at a height substantially level with the conveyor of the preceding drying module 11. The conveyor thus serves to pass each sample, in its respective sieve and on its respective support plate, on to the work-surface 62 of the recording module 12.

The work-surface 62 supports a housing 65 which is positioned immediately adjacent the preceding drying module 11 (to the left as viewed in FIG. 8). The housing has an internal recess (not shown) of similar configuration to the recess provided in the housing 17 of the preparation module 7. The recess is thus sized and configured to receive the support plates 19 of each sample as they are passed to the recording module automatically from the second drying module 11. The housing 65 has a second RFID reader 66 located at its end remote from the preceding drying module 11.

The recording module 12 further comprises a camera 67 which is mounted in a position spaced above the housing 65 by a camera support 68. The camera 67 is oriented in a manner effective to capture images of samples passing below the camera. The camera can take any convenient form. For example, in one embodiment the camera 67 may take the form of a digital single-lens-reflex camera having a close-up (macro) lens 69 fitted with a ring-flash 70. The camera 67 is mounted such that its lens 69 points generally downwardly, and preferably vertically downwardly towards the work-surface 62. Alternatively, the camera could take the form of a 3D camera, and may thus be stereoscopic. The camera is operatively connected to a second computer 71 (which may take the form of a conventional desktop, laptop or notebook computer) having a memory, a display and an input keyboard. The second RFID reader 66 is also operatively connected to the computer 71. The computer 71 on the recording module 12 is operatively connected, for example by a suitable network, to the computer 16 of the preparation module 7.

The recording module 12 also includes a tap or shower head 72 which is supported above the work-surface 62 and which is connected to a supply of clean, and preferably warm water. A basin 73 is provided below the tap or shower head 72 and is supported below the work-surface 62.

The recording stage 6 of the method is performed as follows using the recording module 12. Washed and dried samples are automatically advanced, via the conveyor 29 of the preceding drying module 11, into the recessed housing 25, ready for inspection by an operator or technician. It is possible that during the preceding washing and drying stages some samples may have become scattered around their respective sieves and so the operator or technician is afforded an opportunity manually to arrange the constituent grains into the centre of the sieve ready for photography.

The sieve 25 containing the sample can then be slid, along with its underlying support plate 19, beneath the camera 67. In this position, the RF tag 20 on the support plate 19 becomes aligned with the second RFID reader 66 which identifies the tag and passes that information to the computer 67. The computer then calls up the data pertaining to the sample recorded in the preparation module computer 16 associated with the scanned RF tag 20.

After identification of the sample under the camera 67 by the RFID reader 66 and the logging of that information in the memory of the computer 71, a predetermined period of time elapses (for example 5 seconds) to permit any last minute rearrangement of the sample in the sieve by the operator or technician, and then the camera 67, being controlled automatically by the computer 71, captures an image of the sample in the sieve 25. The image is then automatically associated in the memory of the computer 71 with the data pertaining to the sample for storage and later viewing and analysis of the sample.

A weighing device (not shown), for example in the form of digital scales, may be provided on the recording module for weighing each sample, and is preferably connected to the computer 71. The weight of each sample is thus automatically recorded and logged by the computer and associated with the respective sample. A printer (not shown) may also be connected to the computer 71 for control by the computer so as to print a label displaying the relevant sample data. The sample can then be poured from the sieve 25 into a sample storage bag or the like, and the label affixed to the bag to identify its contents. The empty sieve (and indeed the supporting plate 19 if necessary) can then be rinsed clean of any remaining sample using the shower head 72 and basin, before being returned to the preparation module for reuse with another rock sample.

It is proposed that the operation and control of the entire method and apparatus of the present invention will be handled by bespoke software. The software will be configured to control each of the aforementioned modules, and also to automatically photograph, weigh, and label each sample which is processed by the system.

The above-described method and apparatus of the present invention provide a very efficient and effective way to wash, dry and log a large number of rock samples in a quick, reliable and cost-effective manner. Also, because the apparatus of the preferred embodiment uses multiple washers 34*a*-*d* which are supplied with recycled water previously used for washing samples, the system has a very low water-consumption. This makes the system of the present invention highly advantageous from an environmental point of view.

The enhanced speed and efficiency of the sample cleaning process, in turn, improves the speed and efficiency of the decision-making process for the oil & gas companies, during very costly field operations.

As well as improvements in the speed, efficiency and environmental considerations of the sample washing process, the method of the present invention also allows for improvements in sample labelling and initial sample data capture on-line, such as sample weighing, sample photography and preliminary geotechnical analysis, e.g. XRF analysis.

Whilst the invention has been described above in detail, with specific reference to particular embodiments of the method and apparatus of the invention, it is to be appreciated that various modifications can be made either to the method or to the apparatus without departing from the scope of the invention. For example, whilst the embodiments described in detail above involve the provision and use of support plates 19 to support and carry the individual sieves 25, it is envisaged that in variants of the invention the support plates may not be necessary. For example, it is proposed that the conveyors 29 could each be configured so as to have a plurality of predefined recesses or other formations to receive respective sieves. In such an arrangement either the sieves themselves, or even the conveyor, could carry the RF tags 20 used to identify each sample as it progresses through the apparatus. In the event that the RF tags are mounted to the conveyor, it is envisaged that each tag would be mounted adjacent a respective sieve-receiving recess or the like.

Furthermore, whilst the invention has been described above with reference to an arrangement comprising two successive drying modules 10, 11, it is proposed variants could use on a single drying module. Indeed, it may be convenient for some applications to integrate the aforementioned modules into a single unit. For example, it is proposed that the entire system of the invention could be made so as to be sufficiently compact to fit inside a standard shipping container for convenient transportation. In this manner it is proposed to make the system mobile so that it can be conveniently moved from one site to another, and even for use on offshore drilling rigs.

In variants of the invention it is possible to replace the plurality of discrete and spaced apart dryers with a single, substantially continuous dryer. For example, an elongate oven or drying lamp could be provided through or under which the washed samples are conveyed during the drying stage of the method.

Whilst the invention has been described with reference to an arrangement in which the tanks 39, 53 are each mounted on wheels or casters so as to be removable from their respective modules, it is envisaged that they could instead be formed as integral parts of each module.

When used in this specification and claims, the terms "comprises" and "comprising" and variations thereof mean that the specified features, steps or integers are included. The terms are not to be interpreted to exclude the presence of other features, steps or integers.

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

The invention claimed is:

1. A method of washing rock samples for subsequent studying and derivation of geological information from the rock samples, the method comprising the steps of: providing a plurality of discrete rock samples for deriving the geological information; providing a plurality of sequentially arranged and equi-spaced discrete washers each of which is spaced from a respective washing position and configured to direct a washing flow of water towards said washing position; providing a plurality of sequentially arranged and equi-spaced discrete dryers each of which comprises a heater arranged to direct heat towards a respective drying position; automatically conveying said samples, in succession, relative to said washers in a step-wise manner so that each sample moves through said washing positions for sequential washing by each said washer, wherein each said sample remains stationary, relative to each said washer, in each said respective washing position for an equal and predetermined washing period during which the sample is washed by said respective washing flow of water; and subsequently drying each said sample by automatically conveying said samples, in succession, relative to said dryers in a step-wise manner so that each sample moves through said drying positions for sequential drying by each said dryer, wherein each sample remains stationary, relative to each said dryer, in each respective drying position for an equal and predetermined drying period, each said predetermined drying period being equal in length to each said predetermined washing period; wherein each sample is moved by an index distance between successive said washing periods and is moved by said index distance between successive said drying periods, each said index distance being equal to the distance by which said washers are equi-spaced apart and equal to the distance by which said dryers are equi-spaced apart.

2. The method according to claim 1, comprising supply of fresh water to at least one of said washers.

3. The method according to claim 1, comprising a step of collecting water used to wash said samples in each said washing position and recirculating the water for supply to at least one of said washers.

4. The method according to claim 3, wherein said step of automatically conveying the samples relative to said washers comprises moving each said sample through the washing position associated with the at least one washer supplied with recirculated water before the washing position associated with the at least one washer supplied with fresh water.

5. The method according to claim 3 wherein a plurality of said washers are supplied with recirculated water, and a single washer is supplied with fresh water.

6. The method according to claim 3, further comprising a step of filtering said recirculated water prior to its supply to the at least one washer.

7. The method according to claim 3, further comprising a step of passing said recirculated water over a weir prior to its supply to the at least one washer.

8. The method according to claim 1, further comprising a step of RF tagging each sample.

9. The method according to claim 1, further comprising a step of placing each said sample in a respective receptacle prior to said conveying step, wherein the respective receptacle permits water remaining on the sample to drain.

10. The method according to claim 9, wherein each said receptacle takes the form of a sieve.

11. The method according to claim 1, wherein each said heater comprises an infrared lamp.

12. The method according to claim 1, further comprising a step of automatically agitating each sample as it is dried.

13. The method according to claim 1, further comprising a step of photographing each sample after said drying step.

14. The method according to claim 1, further comprising a step of weighing each sample after said drying step.

15. The method according to claim 1, further comprising a step of labelling each sample after said drying step.

16. The method according to claim 1, wherein the rock samples are small rock fragments from a drilling process, the small rock fragments obtained as ditch cuttings and arriving as dirty fragments of rock covered in drilling mud.

17. The method according to claim 1, comprising a step of labelling the samples with the identity and location of the rock samples for the subsequent studying and derivation of geological information from the rock samples.

* * * * *